United States Patent [19]

Rammler

[11] Patent Number: 5,327,891
[45] Date of Patent: Jul. 12, 1994

[54] CATHETER TRACK AND CATHETER FOR DIAGNOSIS AND TREATMENT

[76] Inventor: David H. Rammler, 30 Oak Hill Dr., Woodside, Calif. 94062

[21] Appl. No.: 922,617

[22] Filed: Jul. 30, 1992

[51] Int. Cl.$^5$ .............................................. A61B 8/12
[52] U.S. Cl. ................................ 128/658; 128/662.02; 604/280
[58] Field of Search ...................... 128/654, 656–658, 128/662.02, 662.05, 662.06, 754; 356/243; 604/280

[56] References Cited

U.S. PATENT DOCUMENTS

| | | |
|---|---|---|
| 4,027,659 | 6/1977 | Slingluff .............................. 128/658 |
| 4,365,251 | 5/1981 | Tickner . |
| 4,411,055 | 10/1983 | Simpson et al. . |
| 4,442,843 | 4/1984 | Rasor et al. . |
| 4,466,442 | 8/1984 | Hilmann et al. . |
| 4,572,203 | 2/1986 | Feinstein . |
| 4,619,274 | 10/1986 | Morrison . |
| 4,718,433 | 1/1988 | Feinstein . |
| 4,748,982 | 6/1988 | Horzewski et al. . |
| 5,040,548 | 8/1991 | Yock . |
| 5,081,997 | 1/1992 | Bosley, Jr. et al. ............ 128/654 X |
| 5,154,179 | 10/1992 | Ratner .............................. 128/656 X |

OTHER PUBLICATIONS

Widder and Simeone (1986) AJR 147:347–352. Microbubbles as a contrast agent for Neurosonography and ultra-sound guided Catheter Manipulation.

*Primary Examiner*—Angela D. Sykes
*Attorney, Agent, or Firm*—Bertram I. Rowland

[57] ABSTRACT

Catheters are provided having a plurality of vanes external to a central core serving as channels for microbubbles. A track may be provided having grooves in which one of the vanes passes, which track provides additional microbubbles, so as to allow for following the movement of the catheter and track by ultrasonic imaging. The catheter provides for reduced abrasion, as well as ease of following the movement of the catheter through the patient's vessels.

10 Claims, 1 Drawing Sheet

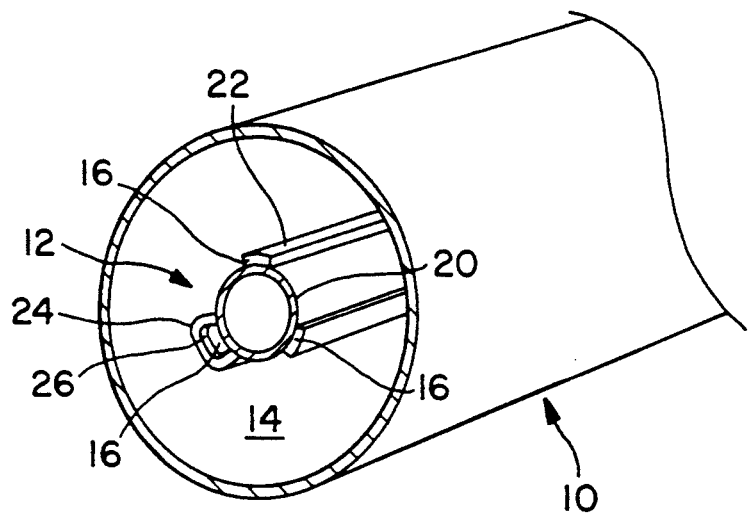
FIG. 1
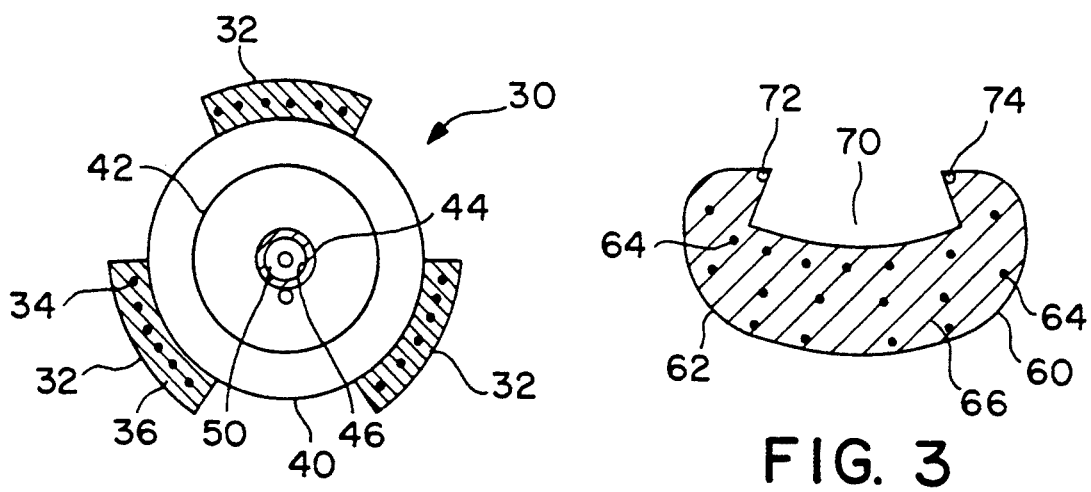
FIG. 2
FIG. 3
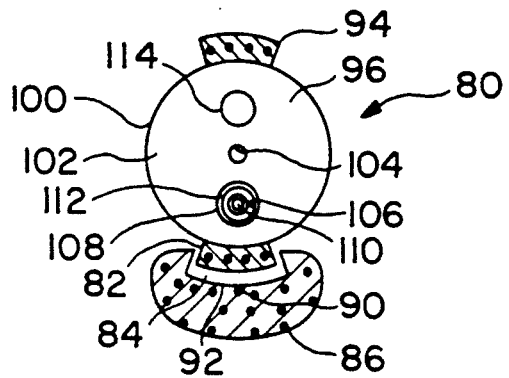
FIG. 4

CATHETER TRACK AND CATHETER FOR DIAGNOSIS AND TREATMENT

INTRODUCTION

1. Technical Field

The field of this invention is catheters.

2. Background

Catheters find extensive use for a wide variety of applications. Catheters have been extensively involved with angioplasty, introducing contrast media, performing biopsies etc. The tubular vessels in the body which serve for the transport of fluids, such as blood, lymph and urine, or ducts, which serve numerous functions, such as the fallopian tube, ducts associated with bladders, and the like, frequently require inspection or treatment at a particular site. Catheters have been developed along with control mechanisms, which allow for movement of long tubes through the vessels, where the ends of the tubes may provide for a variety of procedures. Thus, one may have a balloon which one may expand in the case of angioplasty. Alternatively, one may wish to see a tumor or treat a tumor by introducing a therapeutic agent at the site of the tumor, providing for tubular conduits, optical fibers, lasers, and the like. Other applications may include the detection and/or dissolution of blood clots, injection of diagnostic or therapeutic agents at a particular site, removal of tissue from a particular site, and the like.

The catheter has the capability to deliver a wide variety of materials to a particular site or treat a particular site or remove a sample from a particular site, so long as one can detect where the active end of the catheter is. While an optical fiber may be able to detect the particular environment of the end of the tube, it is not satisfactory to relate the site to other parts of the anatomy. In addition, the flow of blood can interfere with the ability to see the environment in which the optical fiber is present, so that observation may be substantially hindered at such areas.

There is also substantial concern with the injury the catheter may cause as it traverses the blood vessels. For the most part, the exterior of the catheter is round and as it moves through the vessels, makes substantial contacts with the walls of the vessels. This can result in significant abrasion. The situation may be particularly severe, where the catheter goes through one branch of a Y, turns corners, or otherwise must be bent, so as to press against the wall of the vessel.

There is substantial interest in being able to develop improved catheters, so as to allow for accurate detection of the end of the catheter, and/or its course through the body, particularly in relation to site(s) of interest, and to minimize the injurious interactions with the vessel wall.

3. Relevant Literature

U.S. Pat. Nos. 4,265,251, 4,442,843, 4,466,442, 4,572,203 and 4,718,433 describe various ways to prepare bubbles which allow for ultrasonic imaging.

U.S. patents which are illustrative of various catheters and their guiding mechanisms include U.S. Pat. Nos. 5,040,548; 4,748,982; 4,619,274 and 4,411,055.

SUMMARY OF THE INVENTION

Modified catheters and catheter tracks are provided, where the catheters are provided with vanes which serve to minimize contact with vessels through which the catheter progresses and serve as channels for echogenic microbubbles. A track is provided for guiding the catheter, which track also contains echogenic microbubbles. The track has a groove in which a vane can ride and be guided.

BRIEF DESCRIPTION OF THE DRAWINGS

FIG. 1 is a diagrammatic perspective view of the catheter and track in a blood vessel;

FIG. 2 is a cross-sectional view of a catheter;

FIG. 3 is a cross-sectional view of a track; and

FIG. 4 is a cross-sectional view of a catheter in a catheter track.

DESCRIPTION OF THE SPECIFIC EMBODIMENTS

In accordance with the subject invention, novel catheter structures are provided which reduce interaction with vessel walls and provide for detection of the catheter's position, particularly the position of the end of the catheter. The devices of the subject invention achieve this by attaching to the core of the catheter at least two vane-like ducts or channels, which comprise echogenic microbubbles. The vanes serve to minimize contact between the catheter core and the vessel walls. The vanes also house microbubbles, which are echogenic and may serve for ultrasonic detection of their presence in the vessel. In addition, ancillary to the catheter, a catheter track can be provided which can be easily introduced into the vessel and may serve as a guide for a vane which fits into a groove in the tract. The track would also serve as a housing for echogenic microbubbles, so that the catheter and track would provide for a significantly greater ultrasonic signal than either one alone.

Catheters can be provided for a wide variety of purposes, where the core of the catheter may contain one or more flexible elongate tubes, rods, pipes, drug delivery systems and stents, optical fibers, wires, e.g. guide wires, and the like, or where one or more of these may be introduced into the core after the catheter has been guided to a particular site. Particularly, there will be an outer elongate flexible tube whose lumen serves as a passageway for the various components to be used for diagnosis and therapies. The forward end of the catheter, the end first entering the vessel, may contain a wide variety of components to serve a variety of purposes. The forward end may include a deflated balloon for angioplasty where the balloon may be inflated and deflated as required. The end may comprise the orifice of a tube, which allows for the introduction of agents at the terminus of the tube. The end may have the end of an optical fiber which allows for irradiation or illumination, which would allow for visualizing the area surrounding the optical fiber end. For some applications, ultrasonic transducers, light emitting diodes or the like may be employed.

Depending upon the use of the catheter, the catheter core will generally range from about 0.02 to 0.25 in. in outer diameter, more usually about 0.025 to 0.15 in. in outer diameter. With the vane-like attachments, the entire diameter will generally be in range of about 0.03 to 0.3 in., more usually 0.05 to 0.2 in. where the vanes will generally be from about 5 to 50% of the total diameter of the catheter.

Usually, there will be at least two vanes and not more than about four, more usually not more than about three vanes. Each of the vanes may be the same or different, there being at least one vane which will comprise echogenic microbubbles. The vanes will usually extend continuously along substantially the entire length of the catheter, but may be intermittent, being spaced apart, or having one or more vanes which extend from the beginning of the catheter to only a portion of the length of the catheter and comprising echogenic microbubbles. The remaining portion of the catheter could have vanes which are rods or extended ribs, having smooth rounded edges, serving only to prevent contact between the catheter core and the vessel wall.

Generally, the vanes will have less than about 75%, usually less than about 50% of the surface area if the vanes were connected to provide a continuous tubular surface, and usually at least about 20%, more usually at least about 25% of the surface area of a tube having a radius going from the center of the core to the outer perimeter of the vane.

The vanes may be made of any physiologically acceptable material, where the walls will be relatively thin, ranging from about 5 to 100 mils. Materials include polyethylene, nylon, Teflon or other fluorocarbon polymer, combinations thereof and the like. Desirably, the volume contained per inch of length of the catheter will be in the range of about 0.14 in$^3$ to 0 1 in$^3$, where the cross-sectional area of each vane will be 0.14 to 0.1 inch.

Depending upon the function of the vane, the vane may take a variety of shapes. Besides the function of the vanes, other considerations will include ease of manufacturing, cost, stability, their use as a plastic guide visa vis the metal guidewire. The different roles the vanes play may be inconsistent and require various compromises. To maximize the ultrasonic signal, one would wish to have the maximum volume in the vanes. However, one also wishes to minimize the contact between the vane and the vessel wall. Various cross-sectional shapes may be employed, such as trapezoidal, where the short side may be adjacent to the central core or adjacent to the vessel wall, where the side adjacent to the vessel wall is preferably rounded to minimize contact and abrasive injury, conveniently hemispherical. The reflective surface of the catheter will be augmented by the vanes which are at right angles to the circular body of the catheter.

Where the vane need not include the echogenic microbubbles, the vane may take a variety of shapes, particularly as to rods, fins, or the like, where the edge adjacent to the vessel wall can be rounded.

The microbubbles may be prepared by any convenient means and introduced into the channels of the vanes using syringes or other transferring means or mixed with the polymer prior to extension of extrusion. The catheter microbubbles may be pre-prepared or prepared inside the vane as appropriate. Microbubbles may be prepared as described in U.S. Pat. Nos. 4,276,885; 4,572,203; 4,718,433 or 4,442,843 as convenient, or our filing. Microbubbles can be obtained by introducing a gas, e.g. carbon dioxide, into a viscous sugar solution at a temperature above the crystallization temperature of the sugar, followed by cooling and entrapment of the gas in the sugar crystals. Microbubbles can be formed in gelatin and introduced into the vanes. Microbubbles can also be produced by mixing a surfactant, viscous liquid and gas bubbles or gas forming compound, e.g. carbonic acid salt, under conditions where microbubbles are formed.

The media in the vanes and track will normally be a physiologically acceptable medium, and may be aqueous media, gels, particulates in a fluid medium, where the particulates include voids, or the like. The particular manner of forming microbubbles will depend upon the application for the catheter, available equipment, convenience, the microbubble stability required, the size of the microbubbles, and the like. The vanes may have septums, openings at the rear end adjacent to the guiding catheter, or other convenient site for the introduction of the microbubble-containing medium. The presence of the medium in the vanes serves as a cushion when the vanes encounter the vessel wall.

The track will be approximately hemispherical or hemielliptical, generally comprising between about 25 to 60% of the circumference of a circle or ellipse. The track will have a groove in which a vane fits and is able to travel smoothly through the track. Therefore, by initially guiding the track to the desired site and establishing the position of the track, one can then move the catheter through the track, without having to be concerned about the route the catheter takes. One also may follow the catheter through the track by means of ultrasonic imaging and can activate the catheter end at various sites along the track. Thus, a balloon may be inflated or deflated, chemical compounds released, and the like, along the pathway.

The track will generally have a cross-sectional area of about 0.5 to 0.14 inch. As in the case of the vanes, any convenient material may be used which is physiologically acceptable and has the appropriate characteristics. The plastics indicated previously find use. The wall thickness may vary depending on the nature of the material, degree to which the track may be pressurized, ease of fabrication and the like. The track is hollow and will be filled with a liquid or semi-solid medium which will impart various degrees of rigidity to the track. The medium will include microbubbles so that the position of the track may be monitored by ultrasonic imaging.

The track will have from 1 to 2 guide wires to guide the track through the vessel. Guiding systems employed for catheters may be adapted for the track. Thus, the guide wire may be in the lumen of the track, bonded to the bottom of the track or groove, along the upper edges of the track, or at any convenient site which permits guiding the track for the particular application. The guide wire may take the form of a stainless steel wire of about 0.008-0.02 inches diameter and may be coated with an appropriate material, if necessary. The guide wire can be adapted to any of the conventional guiding systems used with conventional catheters.

The subject catheters are highly versatile in their use. One particular application is the treatment of neoproliferative tissue, e.g. cancer, in the vessel. In this embodiment, a laser wand is employed which can be directed to the site of the diseased tissue. Along with the laser wand, a delivery tube attached to a pump is carried in the catheter which can deliver a dye to a site in the vessel. The dye is selected to coat the vessel and have a reasonable residence time. Therefore, one can first introduce the dye, remove the delivery tube and then introduce the laser into the vessel. The presence of the microbubbles allows for precise siting of the various instruments in the vessel.

For further understanding of the invention, the drawings will now be considered. In FIG. 1, a blood vessel 10 is depicted in which catheter 12 extends into the lumen 14 of the blood vessel 10. The catheter 12 has three vanes 16 symmetrically disposed about a central tube 20 where the vanes 16 extend the length of the catheter 12. The vanes 16 are hollow, forming channels 22. In each of the channels 22 is a medium comprising microbubbles. One of the vanes 16 is fitted into track 24 having groove 26 in which the vane 16 can traverse. The track 24 is filled with a medium comprising microbubbles.

In FIG. 2 is catheter 30 with vanes 32 containing microbubbles 34 in a viscous medium 36. The catheter 30 may be used for the introduction of various materials into the lumen of the vascular vessel or other duct. The vanes 34 are attached to annular member 40, which serves as a housing for operative parts of the catheter. Inner-annular member 42 is a dilatable tube which can extend beyond the end of outer annular member 40. Coaxially disposed in the inner annular member 42 are an outer tubular member 44 and an inner tubular member 46 which define flow passage 50. The outer extremities of tubular members 44 and 46 are bonded together to provide a fluid tight seal so that the fluid passage 50 is in communication with the interior of the inflatable inner-annular member 42, where the inflatable inner-annular member is an expanded portion of outer tubular member 44. A flexible tubular member 52 serves to flush air out of the inflatable outer-annular member 42 and allow for venting. For further description, see U.S. Pat. No. 4,411,055.

In FIG. 3, a cross-section of the track is depicted. The track 60 has lumen 62 which contains bubbles 64 in viscous medium 66. The track has groove 70 which serves to house and guide a vane of the catheter. The track 60 has two guide wires 72 and 74, which are attached to a conventional steering mechanism, not shown. The track may be introduced into an appropriate vessel of the cardiovascular system of a patient, e.g. an antecubital vein, and guided to a desired site, monitored by ultrasonic diagnosis. The catheter vane may then be fitted into the track groove and the catheter directed to the desired site, where the movement of the catheter may be followed by the increase in the ultrasonic signal based on the echogenic bubbles in the vanes.

In FIG. 4, the catheter-track combination 80 is shown, where vane 82 is fitted in groove 84 of track 86. Track 86 has a single guide wire 90 underneath the wall 92 which serves as the floor of groove 92. A second vane 94 serves to reduce the contact of the catheter 96 with the vessel walls of the patient. The catheter 96 comprises an outer annular member 100. The vanes 82 and 94 are positioned on opposite sides to the outer surface of the annular member 100. In the lumen 102 of the annular member 100 is a guide wire 104. On one side of the guide wire are coaxial inner tube 106 and outer tube 108, with inner passage 110 and outer passage 112. The other tube 108 is attached to a distensible or inflatable annular segment, not shown. Inner passage 110 is fluid communication with the inflatable annular segment for inflating the inflatable annular segment. On the other side of guide wire 104 is carrier conduit 114, which may be used for other purposes, such as having a retractable surgical knife for biopsy, administering a dye to a site and then allowing passage of a laser beam or optical fiber or the like. Usually, the device for angioplasty will not be combined with elements for other purposes, particularly where the size of the catheter is severely restricted by the size of the vessels through which the catheter passes.

In operation, the subject catheters may be used much like any conventional catheter, using a guiding wire to control the movement of the catheter through various vessels and ducts of the body. However, by employing ultrasonic sound, one may now follow the movement of the catheter through the various vessels, so as to observe the catheter within the patient, be able to define the relationship of the catheter end to the vessel, as well as other organs, and to direct specific treatments to the desired site. The subject catheter therefore substantially reduces injury to the vessels through which it passes, particularly when used in combination with the track, as well as allowing for following the movement of the catheter without requiring dangerous radiation or other undesirable procedures.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cathether system for diagnosis or therapy of a patient comprising:
   (a) a catheter comprising:
      (i) an elongate flexible tube, having a first end for introduction into a vessel of a patient;
      (ii) an outer surface of said elongated flexible tube having affixed thereto at least two spaced apart vanes defining first lumens, said vanes extending a substantial portion along the length of said flexible tube beginning substantially at said first end;
   (b) a track, wherein said track is in a guiding relationship wit one of said vanes, comprising:
      (i) a partially rounded conduit having one side defining a chord having a substantially centrally located groove extending the length of said track and shaped for receiving one of said vanes; and
      (ii) a second lumen in said conduit.

2. A catheter system according to claim 1, wherein said first and second lumens contain an echogenic microbubble containing liquid.

3. A catheter system according to claim 1, wherein said catheter comprises three symmetrically disposed vanes.

4. A catheter system according to claim 1, wherein said vanes and groove have a trapezoidal cross-section.

5. A catheter system according to claim 1, wherein said catheter comprises means for administering a dye to a site in said vessel and means for irradiating said dye.

6. A catheter comprising:
   (i) an elongate flexible tube, having a first end for introduction into a vessel of a patient;
   (ii) an outer surface of said elongate flexible tube having affixed thereto at least two raised, spaced apart vanes defining first lumens, said vanes extending a substantial portion along the length of said flexible tube beginning substantially at said first end and preventing contact between said elongate flexible tube and said vessel.

7. A catheter according to claim 6, wherein said catheter comprises three symmetrically disposed vanes.

8. A catheter according to claim 6, wherein said vanes have a trapezoidal cross-section.

9. A catheter according to claim 6, wherein said catheter comprises means for administering a dye to a site in said vessel and means for irradiating said dye.

10. A track for receiving a catheter comprising an elongate flexible tube and a vane substantially extending the length of said tube, said track comprising:

(i) a partially rounded conduit having one side defining a chord having a substantially centrally located groove extending the length of said track and shaped for receiving said vane;

(ii) a lumen in said conduit; and (iii) an echogenic microbubble containing liquid in said lumen.

* * * * *